United States Patent [19]
Cracraft

[11] Patent Number: 5,370,648
[45] Date of Patent: Dec. 6, 1994

[54] SLIVER AND SPLINTER REMOVAL APPARATUS WITH MAGNIFYING LENS

[76] Inventor: Danny S. Cracraft, 855 Park Ave., Ely, Nev. 89301

[21] Appl. No.: 167,167

[22] Filed: Dec. 16, 1993

[51] Int. Cl.[5] ............... A61B 17/28; A45D 26/00
[52] U.S. Cl. ......................... 606/131; 606/1; 606/205
[58] Field of Search ............... 294/99.2; 7/107, 162, 7/168, 900; 606/1, 131, 133, 205–211; 30/123.6, 131, 142, 143, 145, 146, 191, 193, 194

[56] References Cited

U.S. PATENT DOCUMENTS

| | | | |
|---|---|---|---|
| 1,510,416 | 9/1924 | Pietz et al. | 606/205 |
| 1,842,403 | 1/1932 | Hunsaker | 606/211 |
| 4,390,019 | 6/1983 | Le Veen et al. | |
| 4,542,743 | 9/1985 | Dunn et al. | |
| 4,836,596 | 6/1989 | Owen | 606/211 |
| 4,932,955 | 6/1990 | Merz et al. | |
| 4,971,055 | 11/1990 | von Zeppelin | |
| 5,074,870 | 12/1991 | von Zeppelin | |
| 5,133,737 | 7/1992 | Grismer | 606/205 |
| 5,263,754 | 11/1993 | Coleman | 606/211 |

*Primary Examiner*—Stephen C. Pellegrino
*Assistant Examiner*—Glenn K. Dawson

[57] ABSTRACT

A new and improved sliver and splinter removal apparatus includes a dual-handle, scissors-action clamp assembly which includes a common pivot between respective handle arms and respective clamping arms of the clamp assembly. The respective clamping arms are capable of coming together and clamping in a clamping zone. A magnifying lens assembly is supported by the clamp assembly. The magnifying lens assembly includes a lens, a lens support, and a support strut for supporting the lens and the lens support, such that the support strut supports the lens adjacent to the clamping zone. The support strut for the magnifying lens assembly is supported on the clamp assembly by a pivot connector. The pivot connector that supports the support strut on the clamp assembly is the common pivot between respective handle arms and respective clamping arms of the clamp assembly. The support strut includes a detent, and one of the clamping arms includes a first well for receiving the detent, such that the lens is placed over the clamping zone when the detent is received in the first well. One of the handle arms includes a second well for receiving the detent, such that the lens is placed opposite the clamping zone when the detent is received in the second well. A carrying case is provided for receiving the sliver and splinter removal apparatus.

4 Claims, 2 Drawing Sheets

SLIVER AND SPLINTER REMOVAL APPARATUS WITH MAGNIFYING LENS

BACKGROUND OF THE INVENTION

1. Field of the Invention

The present invention relates generally to medical instruments and, more particularly, to a medical instrument especially adapted for removing slivers and splinters from a persons skin.

2. Description of the Prior Art

The problem of slivers and splinters that become embedded in a person's skin is one that has persisted for many years. Because the slivers and splinters are generally very small, they are usually very difficult if not impossible to grasp with one's fingers or nails. Moreover, because the portions of the slivers and splinters that protrude from the outer surface of the skin are often very short, the slivers and splinters are often difficult to locate and see. In this respect, it would be desirable if a device for removing slivers and splinters were provided that is readily capable of removing small slivers and splinters. In addition, it would be desirable if the device for removing slivers and splinters were capable of assisting in seeing slivers and splinters that are normally difficult to locate and see.

One instrument that is commonly used for removing slivers and splinters is tweezers. A problem associated with tweezers is that the tips of tweezers are highly susceptible to being bent out of alignment. In this respect, it would be desirable if a device for removing slivers and splinters were provided which avoided the use of tweezers.

Aside from tweezers, surgical clamps or hemostats may also be used for removing slivers and splinters. Throughout the years, a number of innovations have been developed relating to medical clamps, and the following U.S. patents are representative of some of those innovations: U.S. Pat. Nos. 4,390,019; 4,542,743; 4,932,955; 4,971,055; and 5,074,870. It is noted, however, that none of the patents cited above disclose the use of a clamp in removing slivers and splinters. Moreover, none of the cited patents discloses a device for facilitating seeing a sliver or splinter.

Thus, while the foregoing body of prior art indicates it to be well known to use devices to aid in the removal of slivers and splinters, the prior art described above does not teach or suggest a sliver and splinter removal apparatus which has the following combination of desirable features: (1) is readily capable of removing small slivers and splinters; (2) assists in seeing slivers and splinters that are normally difficult to locate and see; and (3) avoids the use of tweezers. The foregoing desired characteristics are provided by the unique sliver and splinter removal apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a new and improved sliver and splinter removal apparatus which includes a dual-handle, scissors-action clamp assembly which includes a common pivot between respective handle arms and respective clamping arms of the clamp assembly. The respective clamping arms are capable of coming together and clamping in a clamping zone.

A magnifying lens assembly is supported by the clamp assembly. The magnifying lens assembly includes a lens, a lens support, and a support strut for supporting the lens and the lens support, such that the support strut supports the lens adjacent to the clamping zone. The support strut for the magnifying lens assembly is supported on the clamp assembly by a pivot connector. The pivot connector that supports the support strut on the clamp assembly is the common pivot between respective handle arms and respective clamping arms of the clamp assembly. The support strut includes a detent, and one of the clamping arms includes a first well for receiving the detent, such that the lens is placed over the clamping zone when the detent is received in the first well. One of the handle arms includes a second well for receiving the detent, such that the lens is placed opposite the clamping zone when the detent is received in the second well. A carrying case is provided for receiving the sliver and splinter removal apparatus.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved sliver and splinter removal apparatus which has all of the advantages of the prior art and none of the disadvantages.

It is another object of the present invention to provide a new and improved sliver and splinter removal apparatus which may be easily and efficiently manufactured and marketed.

It is a further object of the present invention to provide a new and improved sliver and splinter removal apparatus which is of durable and reliable construction.

An even further object of the present invention is to provide a new and improved sliver and splinter removal apparatus which is susceptible of a low cost of manufacture with regard to both materials and labor, and which accordingly is then susceptible of low prices of sale to the consuming public, thereby making such sliver and splinter removal apparatus available to the buying public.

Still yet a further object of the present invention is to provide a new and improved sliver and splinter removal apparatus which is readily capable of removing small slivers and splinters.

Still another object of the present invention is to provide a new and improved sliver and splinter removal apparatus that assists in seeing slivers and splinters that are normally difficult to locate and see.

Yet another object of the present invention is to provide a new and improved sliver and splinter removal apparatus which avoids the use of tweezers.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

Figure 1:
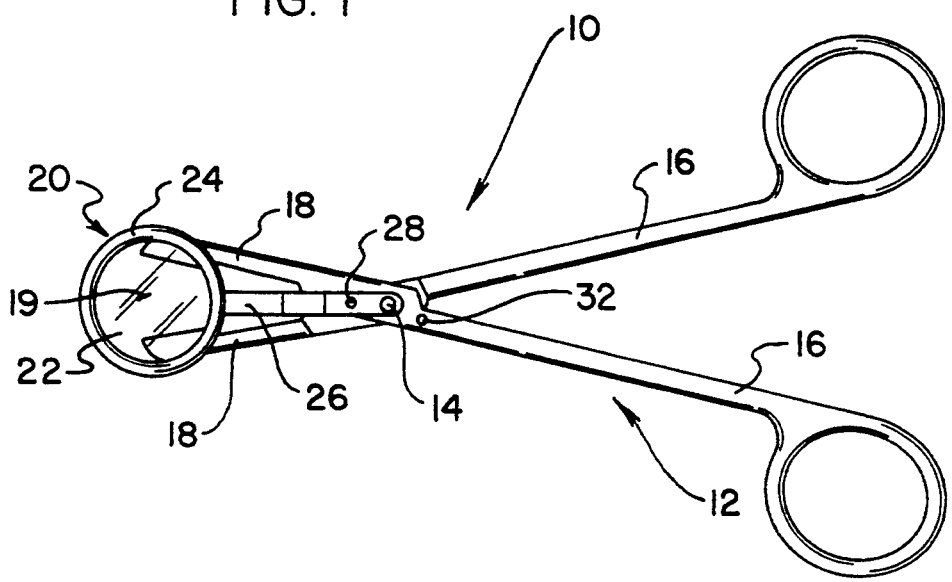
FIG. 1 is a top view showing a first preferred embodiment of the sliver and splinter removal apparatus of the invention.

With reference to the drawings, a new and improved sliver and splinter removal apparatus embodying the principles and concepts of the present invention will be described.

Turning to FIGS. 1-4, there is shown an exemplary embodiment of the sliver and splinter removal apparatus of the invention generally designated by reference numeral 10. In its preferred form, sliver and splinter removal apparatus 10 includes a dual-handle, scissors-action clamp assembly 12 which includes a common pivot 14 between respective handle arms 16 and respective clamping arms 18 of the clamp assembly 12. The respective clamping arms 18 are capable of coming together and clamping in a clamping zone 19.

A magnifying lens assembly 20 is supported by the clamp assembly 12. The magnifying lens assembly 20 includes a lens 22, a lens support 24, and a support strut 26 for supporting the lens 22 and the lens support 24, such that the support strut 26 supports the lens 22 adjacent to the clamping zone 19. The support strut 26 for the magnifying lens assembly 20 is supported on the clamp assembly 12 by a pivot connector. The pivot connector that supports the support strut 26 on the clamp assembly 12 is the common pivot 14 between respective handle arms 16 and respective clamping arms 18 of the clamp assembly 12. The support strut 26 includes a detent 28, and one of the clamping arms 18 includes a first well 30 for receiving the detent 28, such that the lens 22 is placed over the clamping zone 19 when the detent 28 is received in the first well 30. One of the handle arms 16 includes a second well 32 for receiving the detent 28, such that the lens 22 is placed opposite the clamping zone 19 when the detent 28 is received in the second well 32.

Figure 2:
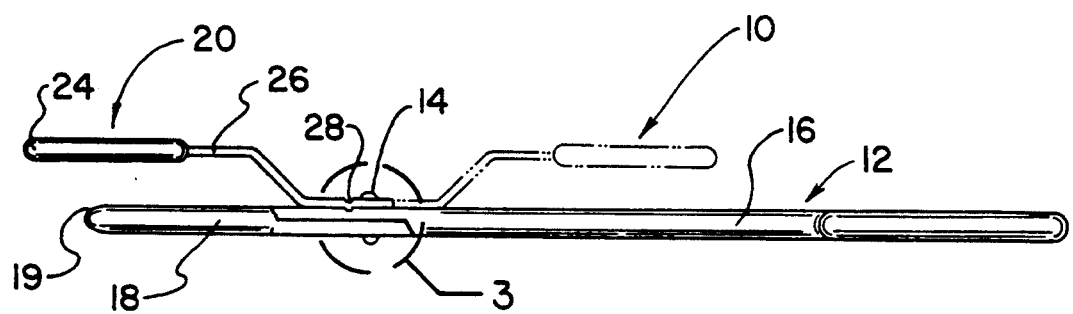
FIG. 2 is a side view of the sliver and splinter removal apparatus shown in FIG. 1.
Figure 3:
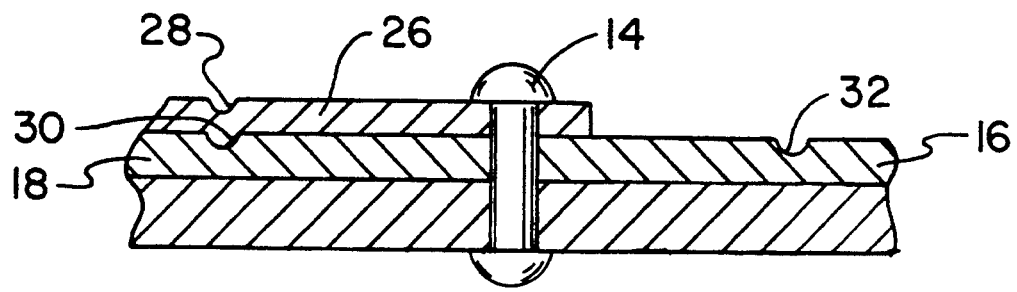
FIG. 3 is an enlarged cross-sectional view of the portion in FIG. 2 that is contained in the circled region 3.

In FIG. 2, the lens 22 is placed over the clamping zone 19 with the magnifying lens assembly 20 shown in solid lines. In contrast, the lens 22 is placed opposite the clamping zone 19 with the magnifying lens assembly 20 shown in broken lines. To go from viewing the clamping zone 19 to not viewing the clamping zone 19, the support strut 26 is merely rotated around the pivot 14.

Although the detent 28 and the first well 30 and the second well 32 can be employed for positioning the lens 22 of the magnifying lens assembly 20, their use is not mandatory. In fact, the support strut 26 can rotate around the pivot 14 a full 360 degrees. In this respect, the lens 22 can be positioned at any position along the complete extent of the 360 degree range of positioning the support strut 26.

Figure 4:
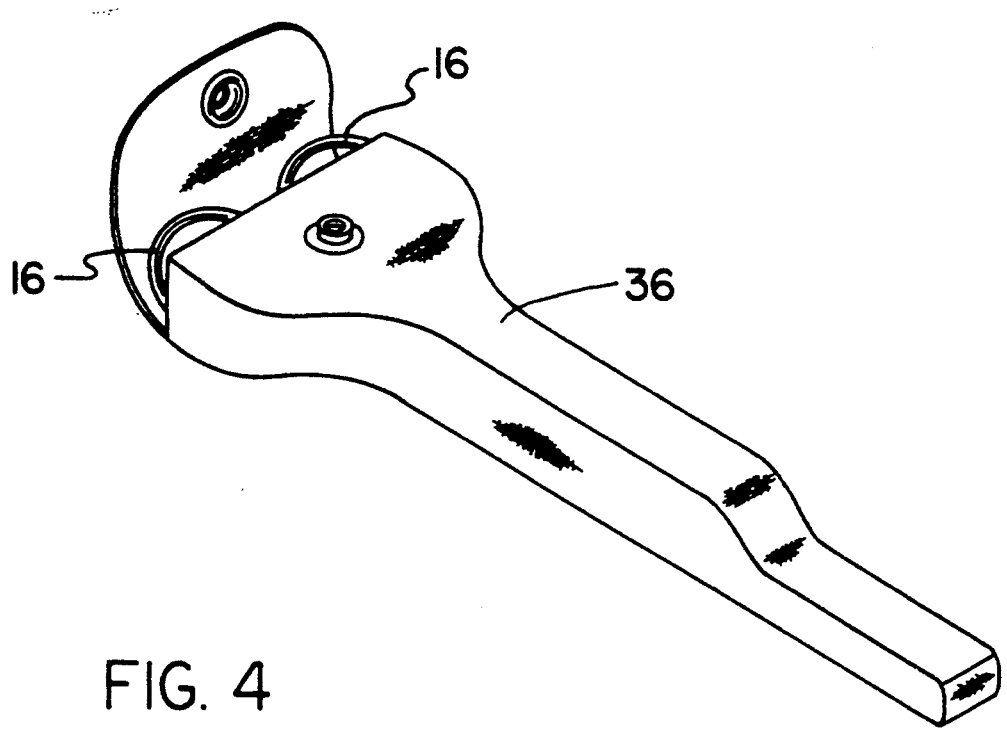
FIG. 4 is a perspective view of the embodiment of the invention shown in FIG. 1 stored in a carrying case.

As shown in FIG. 4, carrying case 36 is provided for receiving the sliver and splinter removal apparatus.

The components of the sliver and splinter removal apparatus of the invention can be made from inexpensive and durable metal, plastic, and cloth materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved sliver and splinter removal apparatus that is low in cost, relatively simple in design and operation, and which may advantageously be used to readily remove small slivers and splinters. With the invention, a sliver and splinter removal apparatus is provided which assists in seeing slivers and splinters that are normally difficult to locate and see. With the invention, a sliver and splinter removal apparatus is provided which avoids the use of tweezers.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by Letters Patent of the United States is as follows:

1. A new and improved sliver and splinter removal apparatus, comprising:
    a dual-handle, scissors-action clamp assembly which includes a common pivot between respective handle arms and respective clamping arms of said clamp assembly, said respective clamping arms being capable of coming together and handle in a clamping zone upon pivotal movement of said respective clamping arms relative to each other and said common pivot point, and
    a magnifying lens assembly supported by said clamp assembly, said magnifying lens assembly including a lens, a lens support, said lens being mounted in said lens support, and a support strut for supporting said lens and said lens support, such that said support strut supports said lens adjacent to said clamping zone,
    wherein said support strut for said magnifying lens assembly is supported on said clamp assembly by a pivot connector,
    wherein said pivot connector for supporting said support strut on said clamp assembly is said common pivot between said respective handle arms and respective clamping arms of said clamp assembly.

2. The apparatus described in claim 1 wherein:
    said support strut includes a detent, and
    one of said clamping arms includes a first well for receiving said detent, such that said lens is placed over said clamping zone when said detent is received in said first well.

3. The apparatus described in claim 2 wherein one of said handle arms includes a second well for receiving said detent, such that said lens is superimposed over said one of said handle arms when said detent is received in said second well.

4. A sliver and splinter removal kit comprising:
    the apparatus described in claim 1, further including:
    a carrying case for receiving said sliver and splinter removal apparatus.

* * * * *